United States Patent [19]
Prather

[11] Patent Number: 5,681,752
[45] Date of Patent: Oct. 28, 1997

[54] METHOD AND APPARATUS FOR DETERMINING THE SIZE AND CHEMICAL COMPOSITION OF AEROSOL PARTICLES

[75] Inventor: Kimberly A. Prather, Riverside, Calif.

[73] Assignee: The Regents of the University of California, Oakland, Calif.

[21] Appl. No.: 435,109

[22] Filed: May 1, 1995

[51] Int. Cl.$^6$ .................................................. G01N 24/00
[52] U.S. Cl. ........................ 436/173; 436/183; 250/281; 250/282; 250/286; 250/287; 250/288; 250/289
[58] Field of Search .................................... 436/173, 183; 250/281, 282, 286, 287, 288, 289

[56] References Cited

U.S. PATENT DOCUMENTS 3,854,321  12/1974  Dahneke ................................. 73/28.01
4,358,302  11/1982  Dahneke ................................. 55/392

OTHER PUBLICATIONS

B. Dahneke *AICHE Symp. Ser.* 1980, 76, 134–143.
J. Marijnissen et al. *J. Aerosol Sci.* 1988, 19, 1307–1310.
O. Kievit et al. *J. Aerosol Sci.* 1992, 23, Suppl. 1, 5301–5304.
J. Allen et al. *Rev. Sci. Instrum.* 1981, 52, 804–809.
J. Marijnissen et al. *Chem. Abstr.* 1989, 110, 100838n.
J. R. Fincke et al. *Plasma Chem. Plasma Proc.* 1993, 13, 579–600.
O. Kievit et al. *Chem. Abstr.* 1993, 119, 11368c.
K.A. Prather et al. *Anal Chem.* 1994, 66, 1403–1407.
T. Nordmeyer et al. *Anal. Chem.* 1994, 66, 3540–3542.
M. V. Johnston et al. *Anal. Chem.* 1995, 67, 721a–727a.
Sinha, M. P., "Laser–Induced Volatilization and Ionization of Microparticles," 1984 American Institute of Physics, Rev. Sci. Instrum. 55(6), Jun. 1984, pp. 886–891.
McKeown, P.J. et al., "On–Line Single–Particle Analysis by Laser Desorption Mass Spectrometry," Analytical Chemistry, vol. 63, No. 18, Sep. 15, 1991, pp. 2069–2073.

*Primary Examiner*—Arlen Soderquist
*Attorney, Agent, or Firm*—James R. Brueggemann; Sheppard, Mullin, Richter & Hampton

[57] ABSTRACT

The invention provides an improved mass spectrometer apparatus, and related method, that characterizes aerosol particles, in real time, according not only to their chemical composition, but also to their size. This added information can be of critical importance when evaluating risks associated with aerosol particles of particular chemical composition. The apparatus achieves this beneficial result in a reliable fashion by first detecting the presence and size of individual aerosol particles moving along a predetermined particle path and by then directing a pulse of high-intensity light at the particle, to desorb and ionize the particle, for analysis of its chemical composition.

39 Claims, 6 Drawing Sheets

METHOD AND APPARATUS FOR DETERMINING THE SIZE AND CHEMICAL COMPOSITION OF AEROSOL PARTICLES

BACKGROUND OF THE INVENTION

This invention relates generally to mass spectrometer apparatus and, more particularly, to apparatus for in situ analysis of aerosol particles in real time, simultaneously determining both the size and the chemical composition of individual particles.

The role of aerosols in atmospheric chemistry has recently become of great interest, because relatively little is known regarding the reactivity and transportation of environmental aerosols. The catalytic effect of aerosol particles in heterogeneous (gas-particle) reactions occurring in the atmosphere is known to depend on both the particle's surface area and the particle's chemical composition; however, current atmospheric models cannot account for, and therefore do not include such reactions.

Aerosol characterization also is important in the medical and industrial fields. Great efforts have been made to study the effects of particles in biological systems, particularly human lungs. Although carcinogenicity and toxicity both depend on chemical composition, the chemical will have little influence on the body unless it is in some way retained. Micron-sized particles are of interest because they are the most likely to serve as carriers of toxic chemicals and to be deposited in human airways for significant time durations. Due to health concerns, industries that require employees to operate in dust-laden environments, e.g., mines, also are interested in aerosol characterization.

Historically, aerosol characterization techniques have analyzed chemically heterogeneous, polydisperse samples and conclusions have been based merely on an average of the particle distribution. This is because few techniques have existed that can perform individual particle analyses. Although information characterizing average particles is helpful, such average particles might not always be the chief instigator in heterogeneous atmospheric reactions or in biological malfunctions. The need, therefore, exists for the characterization of individual aerosol particles, determining both size and chemical composition.

Mass spectrometry is a proven technique for analyzing many types of environmental samples. Mass spectrometry is especially suited for aerosol analysis, because micrometer-sized heterogeneous particles typically contain only about $10^{-12}$ moles of material and thus require a sensitive technique such as mass spectrometry for proper analysis. If combined with some means to determine particle size, mass spectrometry provides an elegant technique for determining both the size and chemical composition of particles in a polydisperse sample. Mass spectrometers generally include four basic steps as part of their analysis: 1) sample introduction, 2) sample volatilization and ionization, 3) mass separation, and 4) ion detection. Numerous routines can be employed to perform each of these steps, although not all are compatible with aerosol characterization. Sample introduction into a mass spectrometer for aerosol characterization commonly is performed in one of two ways: placing the sample on a surface or forming a particle beam by free jet expansion into a vacuum. Sample volatilization and ionization in the case of aerosol mass spectrometric analysis can utilize any of numerous suitable techniques, including for example, laser desorption/ionization. Mass separation also can be accomplished using any of multiple techniques, including for example a time-of-flight mass analyzer. Finally, ion detection can be accomplished using, for example, micro channel plates. Computers can be used for digital storage and display of the resulting data.

As mentioned above, some means for determining particle size ideally is employed in tandem with a mass spectrometer of the kind described briefly above, to provide more useful analytical information. In the past, particle size determination has been accomplished using, for example, electron microscopy, differential mobility analysis, and various optical techniques. However, none of these techniques has yet been effectively integrated with a mass spectrometer to provide simultaneous characterizations of both the size and chemical composition of individual aerosol particles.

A complete characterization of aerosol particles according to both their size and their chemical composition has numerous useful applications. For example, urban areas can be studied for automobile emissions, office buildings for tobacco smoke, and various industrial plants for waste emissions. Natural sources of atmospheric particles, such as volcanic emissions and marine sprays, also are important. In addition to human health concerns, an accurate characterization of atmospheric particles can lead to better a understanding of atmospheric phenomena such as the ozone hole, greenhouse effects, and acid rain. Moreover, a complete characterization of aerosol particles according to both their size and their chemical composition can often lead to a determination of the source of those particles.

It should, therefore, be appreciated that there is a need for a mass spectrometer apparatus for in situ analysis of polydisperse aerosol particles that provides, in real time, both particle size and chemical composition characterization. The present invention fulfills this need.

SUMMARY OF THE INVENTION

The present invention is embodied in an apparatus, and related method, that determines both the size and the chemical composition of individual aerosol particles, in real time. The apparatus includes an aerosol particle accelerator that directs a succession of individual aerosol particles along a predetermined particle path, and further includes an optical detector that detects the speed of individual particles traveling along the path, such detected speed indicating the particle's aerodynamic size. A laser is located downstream of the optical detector and oriented to direct a high-intensity beam of light across the particle path, and a controller controls the laser to so direct the beam coincident with the arrival of individual aerosol particles, such that each particle is desorbed into its component molecules and at least a portion of the desorbed molecules are ionized. Finally, a mass spectrometer such as a time-of-flight mass spectrometer determines the chemical composition of the component molecules associated with each desorbed particle. Thus, in real time, the apparatus can effectively determine both the size and chemical composition of individual aerosol particles.

In a more detailed feature of the invention, the aerosol particle accelerator includes a multi-stage vacuum system, with each stage including a separate vacuum pump and each stage directing individual aerosol particles along the particle path. The vacuum system can include a plurality of concentric tubes that define a series of chambers of progressively increasing vacuum. The chambers are separated from each other by skimmers aligned along the particle path, and the tubes are configured to be adjustably movable axially relative to each other, to vary the distances between the successive skimmers, along the particle path.

In another more detailed feature of the invention, the optical detector can direct first and second beams of light across the particle path, at spaced-apart locations, and can detect light scattered from the particle path by impingement of the first and second beams of light on aerosol particles traveling along the path. A timing device measures the time delay between detection of scattered light from the first beam and detection of scattered light from the second beam, to provide an indication of the associated particle's speed. The first and second beams of light both can be generated by a single laser that generates a beam having multiple wavelengths, in combination with an optical assembly that separates the laser beam into the first and second beams, each having a wavelength different from the other.

The first and second beams of light advantageously can be directed along paths that cross the particle path substantially perpendicular to each other. Aerosol particles thereby are impinged on by both beams only if they travel along a central portion of the particle path, which is necessary to reach a point aligned with the desorption/ionization laser. Scattered light from the first and second beams impinging on an aerosol particle is detected by first and second photodetectors, respectively. The photodetectors are oriented and configured to detect light at a predetermined angle, e.g., 30°, relative to the paths of the incident first and second beams.

The laser that desorbs the aerosol particles advantageously is an Nd:YAG laser that produces pulses of light having sufficient energy to desorb and ionize the successive particles. The laser is controlled to emit each pulse of light when a particle is determined to have arrived at a point along the particle path aligned with the laser, that determination being made based on the detected speed of each aerosol particle, as detected by the optical detector. Optionally, a second laser can be used to ionize the component molecules desorbed from each aerosol particle.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 4 is a perspective view, partially broken away, of the optical system for directing first and second beams of light across the particle path, to detect the speeds of individual particles.

FIG. 5 is a graph depicting the linear relationship between a particle size and its transit time between two fixed points along the particle path.

DESCRIPTION OF THE PREFERRED EMBODIMENT

Figure 1:
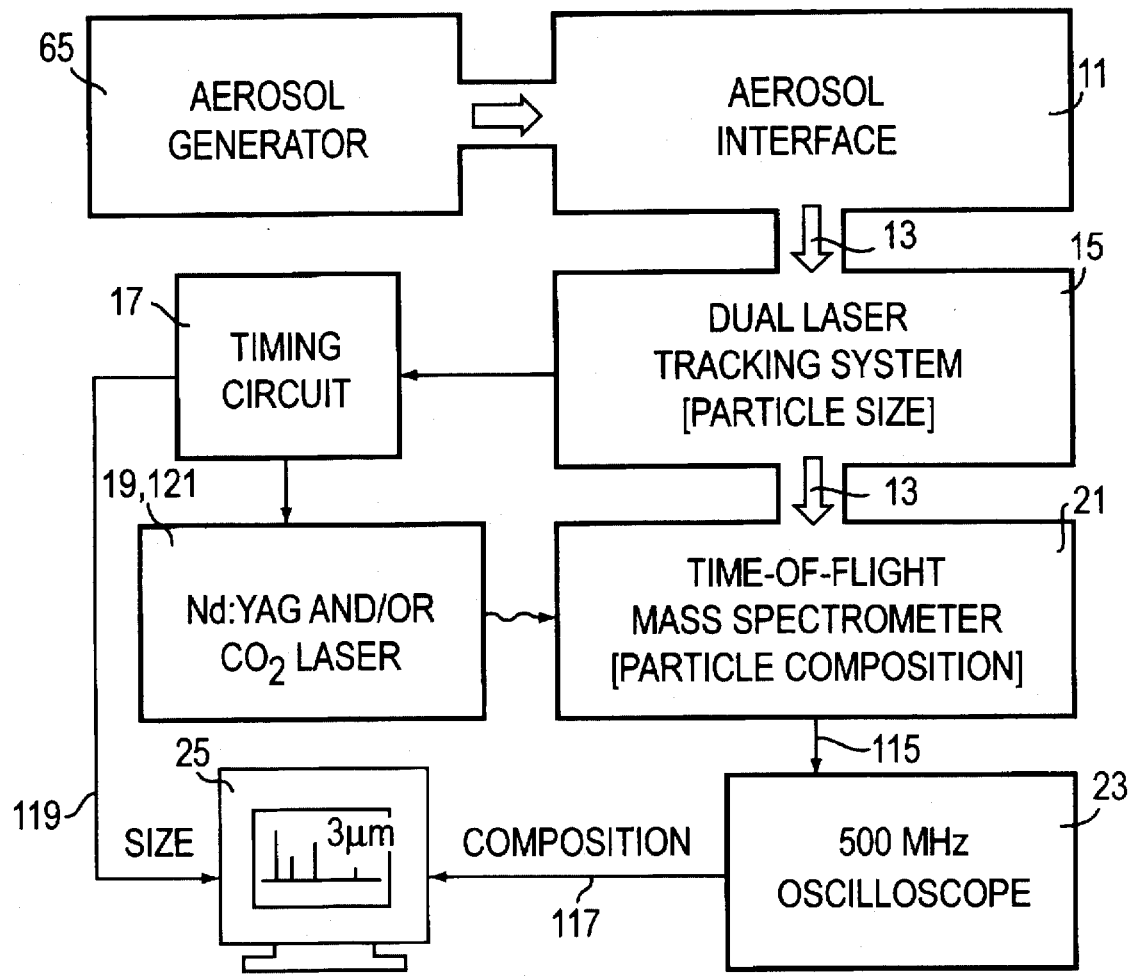
FIG. 1 is a simplified block diagram of apparatus in accordance with a preferred embodiment of the invention, for simultaneously determining both the size and the chemical composition of individual aerosol particles.

With reference now to the drawings, and particularly to FIG. 1, there is shown a block diagram of an apparatus for determining, in real time, both the size and the chemical composition of a succession of aerosol particles. The apparatus includes an aerosol particle interface 11 that accelerates a succession of aerosol particles downwardly in a narrow beam along a generally vertical particle path 13, by supersonic expansion, and a laser beam tracking system 15 that, in conjunction with a timing circuit 17, detects the speed of each particle as it moves along the particle path. The detected speed is a measure of the particle's aerodynamic size. Downstream of the tracking system 15 is a desorption/ionization laser 19, which is conditioned to emit a high-intensity pulse of light towards the particle path, to intercept the particle whose speed was previously detected by the tracking system. This desorbs the particle into its constituent molecules and ionizes at least a portion of those molecules. A time-off-light mass spectrometer 21 then detects the concentrations of the various ionized molecules. A digital oscilloscope 23 and a computer 25 receive signals from the timing circuit 17 and the mass spectrometer 21, to accumulate data representing the size and chemical composition of the successive particles.

Figure 2:
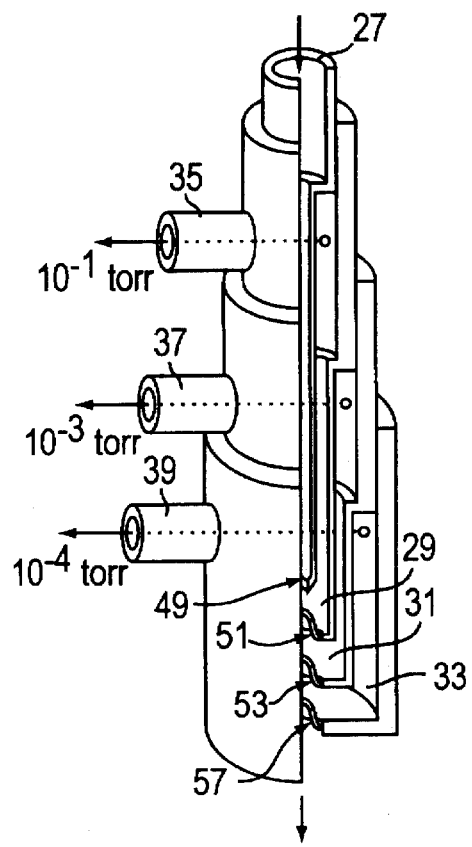
FIG. 2 is a simplified perspective view, partially broken away, of the aerosol particle interface that is part of the apparatus of FIG. 1, for directing a succession of individual aerosol particles downwardly along a vertical particle path.
Figure 3:
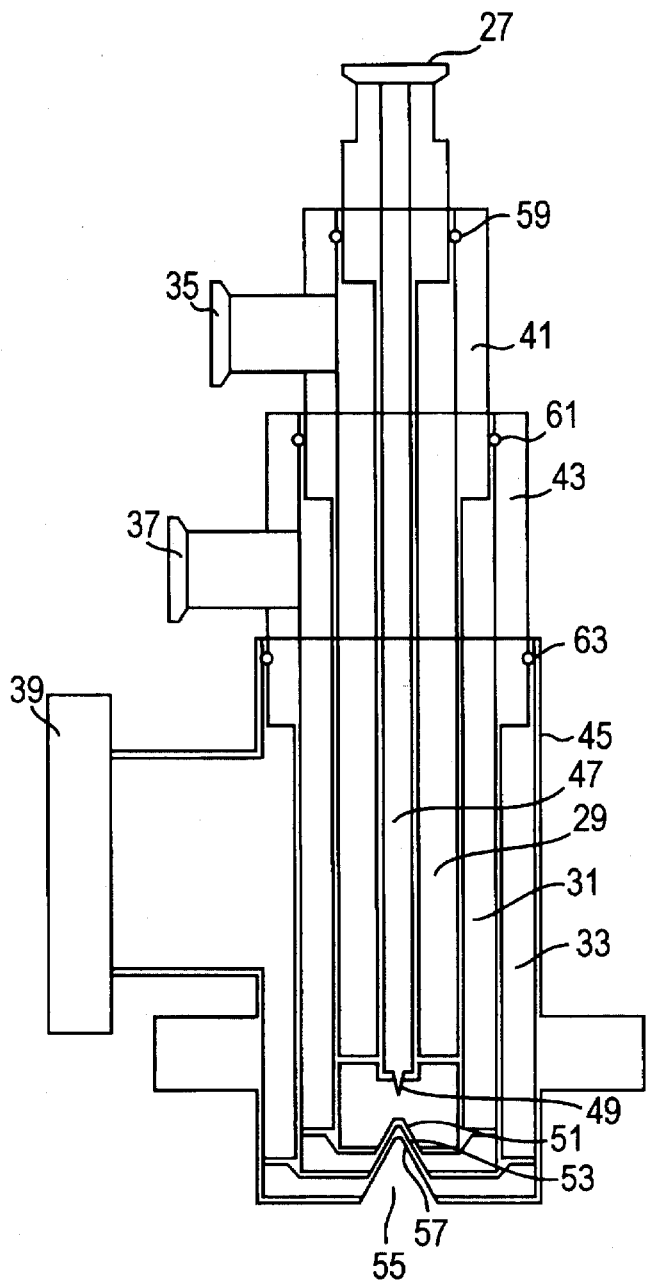
FIG. 3 is a sectional view of the aerosol particle interface of FIG. 2, taken substantially along a verticle section passing diametrically through the interface.

The aerosol particle interface 11 is depicted in greater detail in FIGS. 2 and 3. It includes an inlet port 27 for receiving a gas sample, e.g., air, at atmospheric pressure, and further includes three successive vacuum stages, which are differentially pumped. A first stage reduces the pressure within a first chamber 29 to $10^{-1}$ torr, a second stage reduces the pressure within a second chamber 31 to $10^{-3}$ torr, and a third stage reducing the pressure within a third chamber 33 to $10^{-5}$ torr. These three chambers are connected to vacuum pumps (not shown in the drawings) via outlet ports 35, 37 and 39, respectively. The pumps for the first and second chambers can be mere roughing pumps, while the pump for the third chamber preferably includes a turbomolecular pump backed by a roughing pump.

The chambers 29, 31 and 33 of the three vacuum stages are defined by generally cylindrical walls 41, 43 and 45, respectively, which are configured to be joined together telescopically. A generally cylindrical inlet chamber 47, which receives air from the inlet port 27, is encircled by the three cylindrical chambers.

The cylindrical inlet chamber 47 is separated from the first chamber 29 by a converging nozzle 49 at its lower end. This nozzle directs a small amount of air, including any polydisperse aerosol particles contained in the air, to flow in a narrow beam downwardly along a path, i.e., the particle path 13, toward the first chamber. A flow rate through the nozzle of about 4 cubic centimeters per second is achieved. In turn, the first chamber 29 is separated at its lower end from the second chamber 31 by a first skimmer 51. This skimmer continues to direct a portion of the air along the same particle path. Similarly, the second chamber 31 is separated at its lower end from the third chamber 33 by a second skimmer 53, and the third chamber is separated at its lower end from an outlet chamber 55 by a third skimmer 57. This arrangement results in a stream of aerosol particles being directed along the particle path 13, at speeds that are generally inversely proportional to the particles' aerodynamic size. The outlet chamber is maintained at a pressure of $10^{-7}$ torr.

The skimmers 51, 53 and 57 preferably have orifice sizes of 0.5, 0.5 and 1.0 millimeters, respectively, and they are axially spaced from each other by nominal distances of 0.5, 0.5 and 1.0 centimeters, respectively. The cylindrical walls 41, 43 and 45, which define the respective chambers 29, 31 and 33, are telescopically received within each other, and they are configured so as to be axially movable relative to each other while the chambers are under vacuum. This is achieved using threaded couplings between the walls and O-rings 59, 61 and 63. This enables the axial spacing between the successive skimmers to be controllably adjusted (e.g., over a 3 centimeter range) and thereby improve the collection and linearization of the particles along the particle path 13. This adjustability also can minimize the possibility of size biasing and ensure that a broad range of particle sizes is incorporated into the particle beam.

For use in calibrating the apparatus, an aerosol generator 65 (FIG. 1), which includes a deionizer, is used to generate aerosol particles of predetermined size and chemical composition. Such particles are introduced into the inlet chamber 47 via the inlet port 27, for acceleration along the particle path 13 by the aerosol particle interface 11. This enables the apparatus to be calibrated by directing particles of known size and chemical composition prior to its use to test particles of unknown size and chemical composition received from other sources such as the outside air. Alternatively, the aerosol generator 65, or another aerosol generator, can be used to produce particles for analysis from unknown samples such as soil or liquids.

Located immediately beneath the aerosol particle interface 11 is the laser tracking system 15, which detects the speeds of the successive particles that have been directed along the particle path 13 and now are coasting through the outlet chamber 55. The laser tracking system functions to measure each detected particle's transit time between two spaced locations along the particle path. At this point in the apparatus, each particle has been accelerated to a speed that is inversely related to its aerodynamic size, and it will remain substantially at that speed as it moves through the laser tracking system. The laser tracking system, which is depicted in detail in FIG. 4, includes an Argon-ion laser 67, and an optical system for creating two collimated beams of light 69 and 71, of differing wavelengths, and for directing these two beams paths that intersect the particle path. The beam paths are spaced apart from each other by a distance d, preferably about 5 centimeters.

Figures 4, 5:
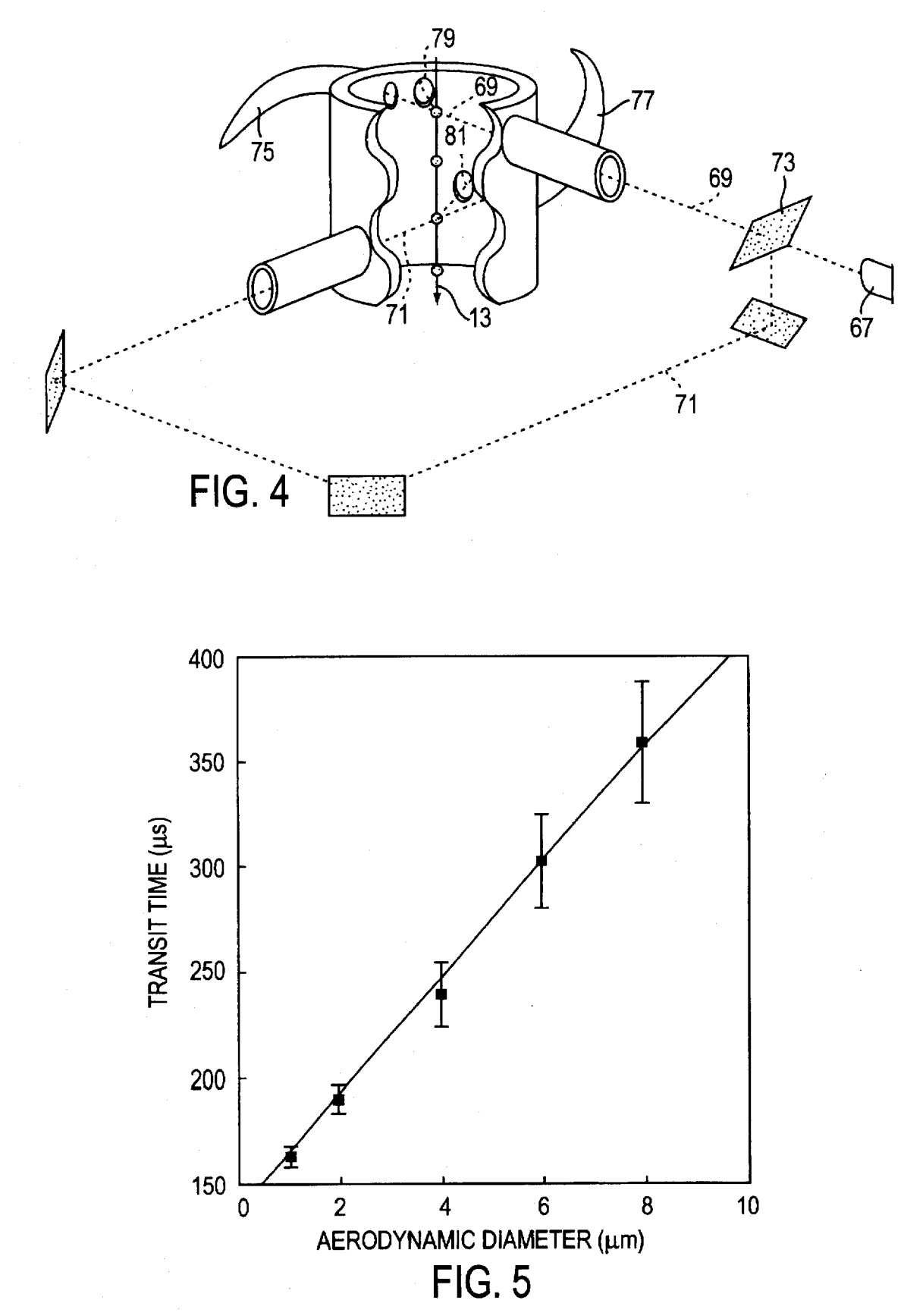

As shown in FIG. 4, this optical system includes a dichroic reflector 73 that transmits the wavelength of the first beam 69 and reflects the wavelength of the second beam 71, along with appropriate mirrors and collimating lenses for directing the beams along their desired paths. It will be appreciated that, alternatively, a second laser, e.g., a Helium-Neon laser, can be used to generate the second beam of light.

If a particle is not present in the path of either the first beam 69 or the second beam 71, the beams will pass through the particle path 13 and will be absorbed by one of two light horns 75 and 77. However, when a particle is impinged on by either the first beam or the second beam, a portion of the light from the impinging beam will be scattered and a portion of that scattered light will be detected by one of two optical sensors, which preferably take the form of photomultiplier tubes 79 and 81. The first photomultiplier tube 79 is oriented in the transverse plane of the first beam of light 69, and it is preceded by an optical system that collects light from the region of the particle path 13 and by an optical filter that transmits only light having the wavelength of that first beam. Similarly, the second photomultiplier tube 81 is oriented in the transverse plane of the second beam of light 71, and it is preceded by an optical system a filter that transmits only light having the wavelength of the second beam.

Collection optics for these two photomultiplier tubes 79 and 81 preferably are oriented to receive light from the general region of the particle path 13, and they are positioned at an angle of about 30° relative to the paths of the respective first and second beams 69 and 71. The paths of the respective first and second beams of light are substantially orthogonal to each other, such that only particles traveling along the very center of the particle path will be impinged on by both beams. This is important, because only particles traveling along the center of the path will reach a point aligned with the Nd:YAG laser 19. This ensures that the laser is triggered only for particles traveling along the center of the particle path, and it minimizes the possibility that the laser will be triggered unnecessarily.

As previously mentioned, one purpose of the laser tracking system 15 is to measure the speeds of the successive particles moving along the particle path 13. Because of the nature of the aerosol particle interface 11, each particle is accelerated to a speed that is generally inversely proportional to its size, and in particular to its aerodynamic diameter. This equates to an approximated linear relationship between each particle's aerodynamic diameter and its transit time between the first and second beams 69 and 71. Another purpose of the laser tracking system is to provide tracking information so that the Nd:YAG laser 19 can be triggered at the particular time that correlates with the arrival of the particle at a position aligned with the laser beam.

A correlation between a particle's transit time and its aerodynamic size can be established experimentally using particles of known size and composition. In FIG. 5, this relationship is shown for $(NH_4)_2SO_4$ particles in the 1–10 micron size range. The error bars in the figure represent one standard deviation of the distribution of velocities imparted to particles of a given size during the expansion process into a vacuum.

The timing circuit 17 measures the speed of each detected particle as it moves along the particle path 13 and conditions the Nd:YAG laser 19 to emit pulses of high-intensity light so as to desorb and ionize the particles when they arrive at a location aligned with the laser. With reference to the block diagram of FIG. 6, the timing circuit includes a counter 83 that is triggered to count upwardly from zero when a particle is detected by the first photomultiplier tube 79 (FIG. 4) to have scattered the first beam of light 69. That upward counting is terminated when that same particle is detected by the second photomultiplier tube 81 (FIG. 4) to have scattered the second beam of light 71. The count stored in the counter at that time indicates the particle's transit time between the two beams.

A first pulse height discriminator 85 receives a detection signal on line 87 from the first photomultiplier tube 79, and it compares this detection signal with a predetermined threshold and produces a START pulse when the threshold is exceeded. Ordinarily, this occurs only when a particle traveling along the particle path 13 has in fact scattered the first beam of light 69. This START pulse is transmitted on line 89 to the counter 83, to initiate its upward count from zero. The counter counts clock pulses received on line 91 from clock 93.

Similarly, a second pulse height discriminator 95 receives a detection signal on line 97 from the second photomultiplier tube 81, and it compares this detection signal with a predetermined threshold and produces a STOP pulse when the threshold has been exceeded. This ordinarily occurs only when a particle traveling along the particle path has scattered the second beam of light 71. This STOP pulse is transmitted on line 99 to the counter 83, to terminate its upward count.

The Nd:YAG laser 19 is positioned such that the pulses of light it emits intersect the particle path 13 at a point downstream of the point of intersection of the second beam of light 71 by a distance 3d, which in the preferred embodiment is 15 centimeters. This distance is exactly three times the distance between the second beam of light and the first beam of light 69. This spacing provides an advance warning of the need to trigger the Nd:YAG laser, which is required for proper operation. The actual triggering of the laser, so that it emits a pulse of light coincident with the arrival of the detected particle at an aligned location, is accomplished by conditioning the counter to decrement to zero upon receipt of a STOP pulse on line 99 from the second pulse height discriminator 95, at a rate one third that of the count up rate. Since the particle is presumed to be traveling at a substantially uniform speed through the evacuated chamber 55, the counter reaches a count of zero when the particle has reached a point on the particle path 13 that is aligned with the Nd:YAG laser. If a laser is used that does not require such an advance warning (e.g., a $CO_2$ laser, $N_2$ laser, or excimer laser), its distance from the second beam of light, of course, can be reduced.

A comparator 101 monitors the count currently stored in the counter 83, received via lines 103, with a count of zero. When a coincidence is detected, it is determined that the detected particle has by then reached a point on the particle path that is aligned with the Nd:YAG laser 19, and the comparator outputs a trigger pulse for coupling through an OR gate 105 to the laser.

Figure 8:
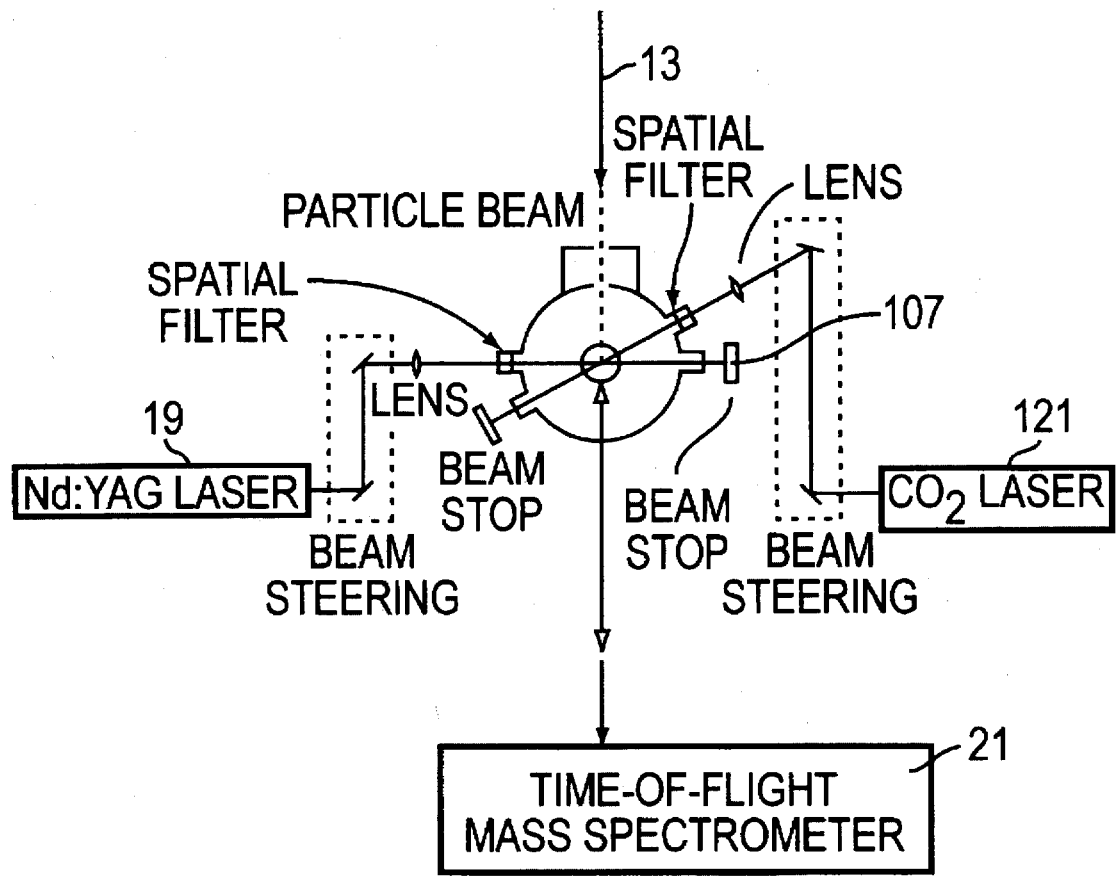
FIG. 8 is a simplified elevational view of the laser desorption/ionization portion of the apparatus of FIG. 1.

The Nd:YAG laser 19 has a minimum operating pulse frequency to ensure stability. Consequently, if an aerosol particle has not been detected within a predetermined time period, the timing circuit 17 outputs an output pulse to trigger the laser to emit a pulse, anyway. Since a particle should not at that time be aligned with the laser, the emitted pulse ordinarily will pass through the particle path 13 and be absorbed by a light horn 107 (FIG. 8). To achieve this result, the timing circuit further includes a minimum frequency override circuit 109, which outputs a trigger pulse whenever it is determined that the laser has not been triggered for a time period corresponding to its minimum frequency. The OR gate 105 ORs together the trigger pulses output by this override circuit and by the comparator 101, to produce the output pulses supplied on line 111 from the timing circuit 17 to the Nd:YAG laser 19. The override circuit 109 is reset by any pulses output by the comparator.

After the counter 83 has been triggered by a START pulse to begin incrementing, but before a STOP pulse has been generated and the counter has decremented to zero, the counter should be disabled from being triggered by any further START pulses. A disable input therefore is provided on line 113 to the first pulse height discriminator 85, and all pulses received by the discriminator from the first photomultiplier tube 79 are disregarded during this time.

Figure 6:
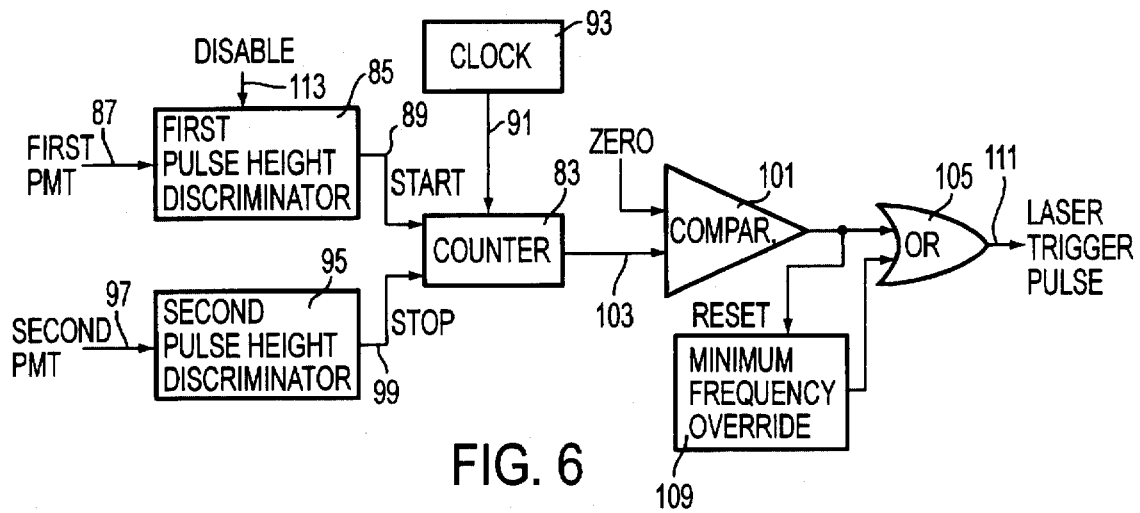
FIG. 6 is a simplified block diagram of the timing circuit of FIG. 1, which detects the speeds of individual aerosol particles and generates control pulses to condition the Nd:YAG laser to emit pulses of light.

For clarity of understanding, the timing circuit 17 is depicted in FIG. 6 in the form of a hardware-type block diagram; however, the circuit preferably is implemented in software. Those skilled in the art will be readily capable of implementing a software program to carry out the defined functions.

It will be appreciated that a situation can occur where different particles will be impinged on by the respective first and second beams of light 69 and 71, yet the timing circuit 17 will mistakenly operate as though just a single particle had been detected. This can occur, for example, when the first beam impinges on a first, relatively slow-moving particle, and the second beam thereafter impinges on a second, relatively fast-moving particle that overtook and passed the first particle. When this occurs, the timing circuit will improperly calculate the particle's speed, and it will trigger the Nd:YAG laser 19 to emit a pulse of light at a time when no particle is aligned with the laser. The pulse of light, therefore, will simply pass through the particle path 13 without impinging on any particle at all, i.e., coincidence error. Although no data will be generated by the subsequent mass spectrometer, that situation is preferred to the situation of prior apparatus of this kind, in which erroneous data was generated.

Figure 7:
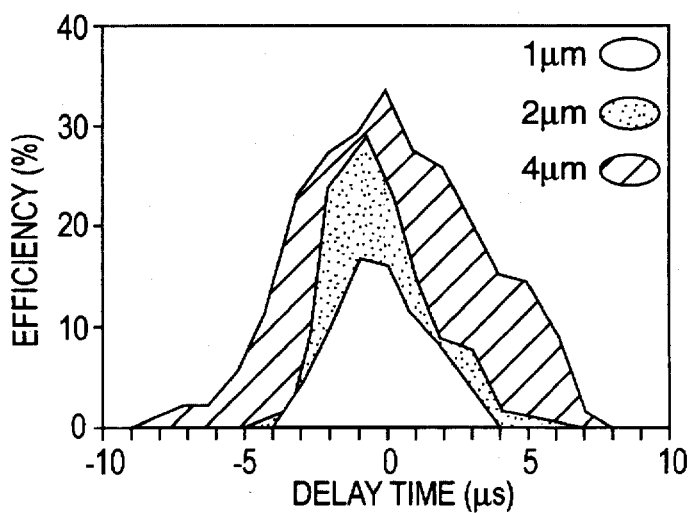
FIG. 7 is a graph showing desorption efficiency as a function of particle size and relative timing of the laser pulse relative to actual arrival of the particle at a point along the particle path aligned with the laser.

FIG. 7 is a graph depicting the efficiency of the timing circuit 17 in determining the arrival of a particle to coincide with a pulse of light from the Nd:YAG laser 19, for 2,4-dihydroxybenzoic acid particles having sizes of 1.0, 2.0 and 4.0 microns. The percentage of particles sized and tracked by the circuit for which a corresponding mass spectrum was obtained is shown as a function of the timing of the laser pulse and arrival of the particle at a position aligned with the laser. Generating the laser pulse either before or after the arrival of the particle decreases the probability for ionization. The fact that the optimum time delay is the same for both large and small particles demonstrates the ability of the apparatus to analyze polydisperse samples; if the interception time were calculated incorrectly, the peak center would shift with particle size, i.e., particle velocity.

When a pulse of light from the Nd:YAG laser 19 does, in fact, impinge on the particle whose speed was detected by the laser tracking system 15 and timing circuit 17, the particle is desorbed into its constituent molecules. The pulse of light has a wavelength of about 266 nanometers and its energy level is sufficient to ionize a significant proportion (typically, about 1%) of the particle's constituent molecules. Non-ionized molecules will be pumped away, while the ionized molecules will be drawn laterally away by the electric field of the time-of-flight mass spectrometer 21. These ions are accelerated to a substantially constant kinetic energy, separating from each other according to their mass/charge ratios. An electrostatic mirror, or reflection, that is part of the mass spectrometer reflects the ionized molecules back, to increase the spectrometer's resolution.

Figure 9:
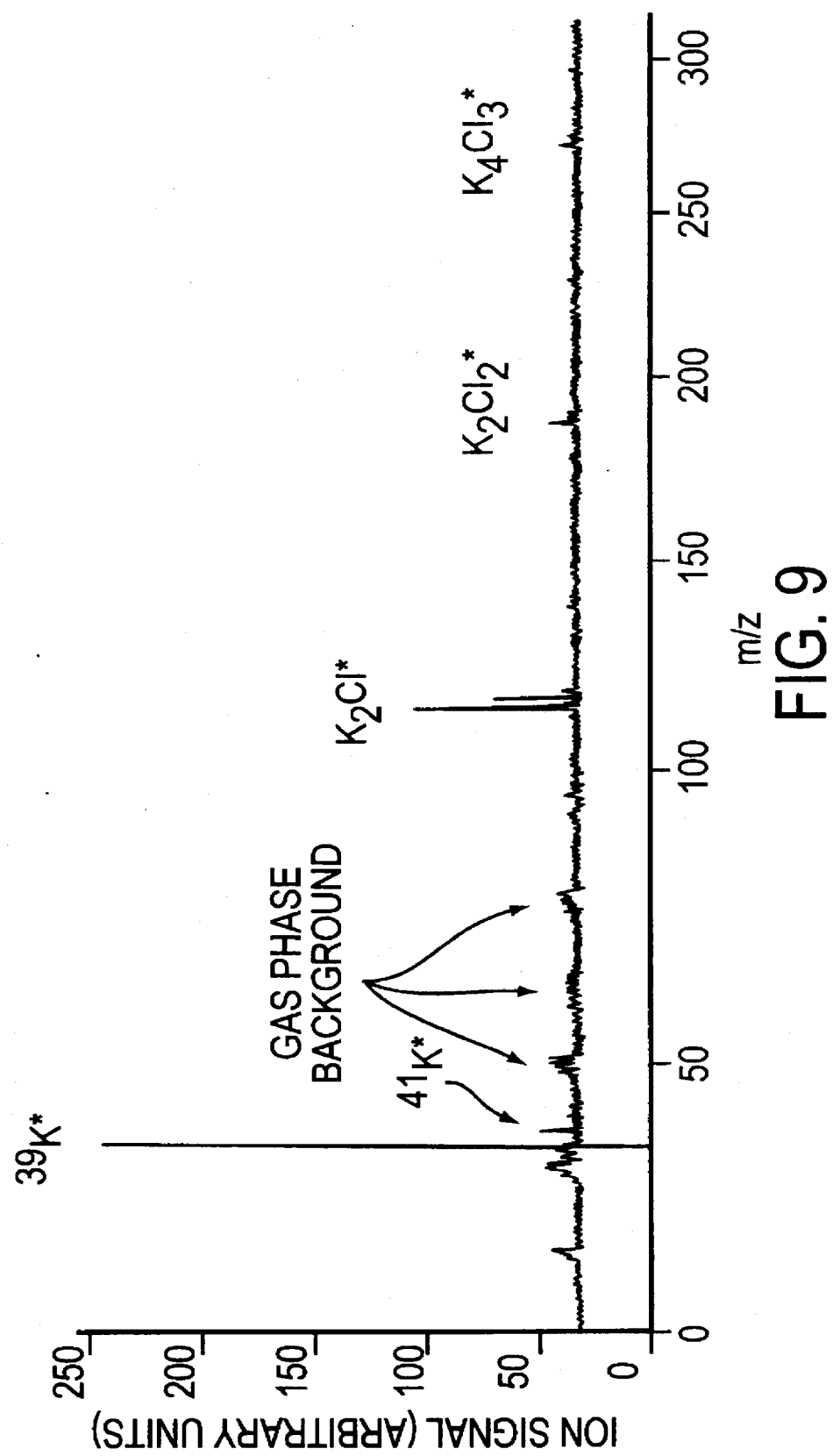
FIG. 9 is a graph of a sample mass spectrum for a single 0.7-micron KCl/2,5-dihydroxybenzoic acid particle produced by the apparatus of FIG. 1.

The time-of-flight mass spectrometer 21, which can be a commercially available apparatus such as is available from Russ Jordan Co., provides an output signal that indicates the distribution of ionized molecules as a function of mass/charge ratio. An example of one such output signal generated for a single 0.7-micron KCl/2,5-dihydroxybenzoic acid particle is depicted in FIG. 9. It shows several signal peaks corresponding to ionized potassium molecules and to several isotopic combinations of chlorine and potassium. Those skilled in the relevant art will appreciate how to interpret such signals and to determine the chemical composition of the desorbed particle. The time-of-flight mass spectrometer can be selectively configured to measure positive ions and negative ions.

With reference again to FIG. 1, the output signal from the time-of-flight mass spectrometer 21 is transmitted on line 115 to the digital oscilloscope 23, and in turn on line 117 to a computer 25, which correlates the chemical composition data represented by the signal with the size information it receives on line 119 from the timing circuit 17 for the corresponding particle. The computer accumulates this data for a great number of aerosol particles, so that meaningful information can be determined for the air sample being analyzed. In normal operation, and at high particle concentrations, the apparatus can accumulate data for about 600 particles during each minute of operation.

In some circumstances, the Nd:YAG laser 19 will fail to ionize a sufficient number of desorbed molecules for effective operation of the time-of-flight mass spectrometer 21. The apparatus, therefore, can further include a supplementary $CO_2$ laser 121 (FIG. 8) that is triggered to emit a pulse of light (at about 10.6 microns) to desorb each particle, and the Nd:YAG laser is then triggered immediately thereafter (e.g., one microsecond later), to ionize the desorbed molecules. The two pulses of light, together, if properly timed, ordinarily will produce sufficient ions to enhance the mass spectrometer's effectiveness. In this alternative embodiment, the laser power levels can be reduced substantially below the level required if just a single laser is being used both for desorption and ionization, thereby reducing the amount of fragmentation of resulting ions.

It should be appreciated from the foregoing description that the invention provides an improved mass spectrometer apparatus that characterizes aerosol particles, in real time, according not only to their chemical composition, but also to their size. This added information can be of critical importance when evaluating risks associated with particles of particular chemical composition. The apparatus achieves this beneficial result in a reliable fashion by first detecting the presence and size of individual aerosol particles and by then directing a pulse of high-intensity light at the particle, to desorb and ionize it for analysis of its chemical composition.

Although the invention has been described in detail with reference only to the preferred embodiment, those skilled in the art will appreciate that various modifications can be made without departing from the invention. Accordingly, the invention is to defined only with reference to the following claims.

I claim:

1. Apparatus for determining the size and chemical composition of individual polydisperse aerosol particles, in real time comprising:

a particle accelerator that directs a succession of individual polydisperse aerosol particles along a predetermined particle path;

an optical detector, disposed along the particle path, that detects the speed of individual polydisperse aerosol particles traveling along the path and produces a corresponding timing signal for each detected particle, wherein the detected speed of each particle indicates the particle's aerodynamic size;

a laser oriented to direct a beam of light across the particle path, separate from and downstream of the optical detector;

a controller, responsive to each timing signal produced by the optical detector, that controls the laser to direct the beam of light across the particle path coincident with the arrival of each aerosol particle whose speed is detected by the optical detector, such that each particle is desorbed into its component molecules; and a mass spectrometer that determines the chemical composition of the component molecules associated with each desorbed particle.

2. Apparatus as defined in claim 1, wherein the particle accelerator includes a multiple-stage vacuum system, each stage of the system including a vacuum pump and each stage directing individual aerosol particles along the particle path.

3. Apparatus as defined in claim 2, wherein:

the multiple-stage vacuum system includes a plurality of concentric tubes supporting a vacuum of progressively increasing amount;

the plurality of concentric tubes are separated from each other by skimmers aligned along the particle path; and the plurality of concentric tubes are configured to be adjustably movable axially relative to each other, to vary the distances between the successive skimmers, along the particle path.

4. Apparatus as defined in claim 1, wherein the optical detector includes:

a first light source that directs a first beam of light across the particle path, at a first predetermined location;

a first detector that detects light scattered from the particle path due to impingement of the first beam of light on an aerosol particle traveling along the path;

a second light source that directs a second beam of light across the particle path, at a second predetermined location, downstream of the first predetermined location;

a second detector that detects light scattered from the particle path due to impingement of the second beam of light on an aerosol particle traveling along the path; and a timing device for measuring the time delay between detection of scattered light by the first detector and detection of scattered light by the second detector, such time delay indicating the speed of the associated particle.

5. Apparatus as defined in claim 4, wherein the first and second light sources together include:

a laser that generates a laser beam having multiple wavelengths; and an optical assembly that separates the laser beam into the first and second beams of light, each having a wavelength different from the other, and that directs the first and second beams of light across the particle path, at the respective first and second predetermined locations.

6. Apparatus as defined in claim 4, wherein the first and second light sources direct the respective first and second beams of light along paths that are substantially perpendicular to each other and that are in transverse planes that are substantially perpendicular to the particle path, such that aerosol particles are impinged on by both beams only if they travel along the center of the particle path.

7. Apparatus as defined in claim 6, wherein:

the first detector includes a first photodetector oriented to detect light received in the transverse plane of the first beam of light, from the direction of the particle path, at a predetermined angle relative to the path of the first beam of light; and the second detector includes a second photodetector oriented to detect light received in the transverse plane of the second beam of light, from the direction of the particle path, at a predetermined angle relative to the path of the second beam of light.

8. Apparatus as defined in claim 7, wherein the predetermined angles between the path of the first beam of light and the path of light received by the first photodetector, and between the path of the second beam of light and path of light received by the second photodetector, both are about 30 degrees.

9. Apparatus as defined in claim 4, wherein:

the laser is oriented to direct a beam of light across the particle path at a location downstream of the second predetermined location by a distance that is substantially the same as the distance between the first predetermined location and the second predetermined location;

the timing device includes a counter whose count is periodically incremented from an initial count after a particle has been detected by the first detector and whose count is periodically decremented after the particle has been detected by the second detector; and the controller controls the laser to direct the beam of light across the particle path when the counter's count returns to its initial count.

10. Apparatus as defined in claim 1, wherein the laser is an Nd:YAG laser that produces pulses of light having sufficient energy to desorb the successive aerosol particles.

11. Apparatus as defined in claim 1, wherein the controller is configured to control the laser to emit pulses of light and to direct a pulse of light when, based on the detected speed of each aerosol particle as detected by the optical detector, that particle is determined to have arrived at a point along the particle path aligned with the laser.

12. Apparatus as defined in claim 1, and further including a second laser that ionizes the component molecules of each desorbed particle.

13. Apparatus as defined in claim 1, wherein the mass spectrometer is a time-of-flight mass spectrometer.

14. Apparatus for determining the size and chemical composition of individual polydisperse aerosol particles, in real time, comprising:

means for directing a succession of individual polydisperse aerosol particles along a predetermined particle path;

means for detecting the location and size of individual polydisperse aerosol particles traveling along the particle path;

laser means located separate from and downstream of the detecting means for directing a beam of light at the successive aerosol particles detected by the means for detecting after a suitable time delay to desorb each particle into its component molecules and to ionize at least a portion of such molecules; and mass spectrometer means for determining the chemical composition of the ionized molecules associated with each desorbed particle.

15. Apparatus as defined in claim 14, wherein:

the means for directing includes a multiple-stage vacuum system, each stage of the system including a vacuum pump and each stage directing individual aerosol particles along the particle path;

the multiple-stage vacuum system includes a plurality of concentric tubes supporting a vacuum of progressively increasing amount;

the plurality of concentric tubes are separated from each other by skimmers aligned along the particle path; and the plurality of concentric tubes are configured to be adjustably movable axially relative to each other, to vary the distances between the successive skimmers, along the particle path.

16. Apparatus as defined in claim 14, wherein the means for detecting includes:

first detection means for directing a first beam of light across the particle path, at a first predetermined location, and for detecting light scattered from the particle path due to impingement of the first beam of light on an aerosol particle traveling along the path;

second detection means for directing a second beam of light across the particle path, at a second predetermined location, downstream of the first predetermined location, and for detecting light scattered from the particle path due to impingement of the second beam of light on an aerosol particle traveling along the path; and timing means for measuring the time delay between detection of scattered light by the first detection means and detection of scattered light by the second detection means, such time delay indicating the speed of the associated particle.

17. Apparatus as defined in claim 16, wherein the first and second detection means together include:

a laser that generates a laser beam having multiple wavelengths; and an optical assembly that separates the laser beam into the first and second beams of light, each having a wavelength different from the other, and that directs the first and second beams of light across the particle path, at the respective first and second predetermined locations.

18. Apparatus as defined in claim 16, wherein the first and second detection means are configured to direct the respective first and second beams of light along paths that are substantially perpendicular to each other and that are in transverse planes oriented substantially perpendicular to the particle path, such that aerosol particles are impinged on by both beams only if they travel along the particle path.

19. Apparatus as defined in claim 16, wherein:

the laser means is oriented to direct a beam of light across the particle path at a location downstream of the second predetermined location by a distance that is substantially the same as the distance between the first predetermined location and the second predetermined location;

the timing means includes a counter whose count is periodically incremented from an initial count after a particle has been detected by the first detection means and whose count is periodically decremented after the particle has been detected by the second detection means; and the laser means is configured to direct the beam of light across the particle path when the counter's count returns to its initial count.

20. Apparatus as defined in claim 14, wherein the laser means includes an Nd:YAG laser that produces pulses of light having sufficient energy to desorb the successive aerosol particles.

21. Apparatus as defined in claim 14, wherein:

the means for detecting is configured to detect the speed of a succession of particles traveling along the particle path; and the laser means is configured to emit pulses of light and to direct a pulse of light when, based on the detected speed of each aerosol particle as detected by the means for detecting, that particle is determined to have arrived at a point along the particle path aligned with the laser means.

22. A method for determining the size and chemical composition of individual polydisperse aerosol particles, in real time, comprising:

directing a succession of individual polydisperse aerosol particles along a predetermined particle path;

detecting aerodynamic size of individual polydisperse aerosol particles traveling along the particle path at a detection location;

directing a collimated beam of light at the successive aerosol particles detected in the element of detecting, at a location downstream of the detection location, and after a suitable time delay, to desorb each particle into its component molecules and to ionize at least a portion of such molecules; and determining the chemical composition of the ionized molecules associated with each desorbed particle.

23. A method as defined in claim 22, wherein:

directing includes using a multiple-stage vacuum system to direct the aerosol particles along the particle path;

the successive stages of the vacuum system are separated from each other by skimmers aligned along the particle path; and directing includes adjustably moving the skimmers axially relative to each other, to vary the distances therebetween, along the particle path.

24. A method as defined in claim 22, wherein detecting includes:

directing a first beam of light across the particle path, at a first predetermined location, and detecting light scattered from the particle path due to impingement of the first beam of light on an aerosol particle traveling along the path;

directing a second beam of light across the particle path, at a second predetermined location, downstream of the first predetermined location, and detecting light scattered from the particle path due to impingement of the second beam of light on an aerosol particle traveling along the path; and measuring the time delay between detection of scattered light from the first beam of light and detecting scattered light from the second beam of light, such time delay indicating the speed of the associated particle.

25. A method as defined in claim 24, wherein directing the first and second beams of light together include:

generating a laser beam having multiple wavelengths; and separating the laser beam into the first and second beams of light, each having a wavelength different from the other.

26. A method as defined in claim 25, wherein directing the first and second beams of light includes directing the beams along paths that are substantially perpendicular to each other and that are in transverse planes oriented substantially perpendicular to the particle path, such that aerosol particles are impinged on by both beams only if they travel along the center of the particle path.

27. A method as defined in claim 24, wherein:

directing the collimated beam of light includes directing the collimated beam across the particle path at a location downstream of the second predetermined location by a distance that is substantially the same as the distance between the first predetermined location and the second predetermined location;

measuring includes periodically incrementing the count in a counter from an initial count after impingement of the first beam on a particle has been detected and periodically decrementing the count in the counter after impingement of the second beam on the particle has been detected; and directing the collimated beam of light occurs when the counter's count returns to its initial count.

28. A method as defined in claim 22, wherein:

detecting includes detecting the speed of a succession of particles traveling along the particle path; and directing a collimated beam of light includes emitting pulses of light and directing a pulse of light when, based on the detected speed of each aerosol particle provided in detecting, that particle is determined to have arrived at a point along the particle path aligned with the beam of light.

29. Apparatus for determining the size and chemical composition of individual aerosol particles, in real time, comprising:

a particle accelerator that directs a succession of individual aerosol particles along a predetermined particle path wherein the particle accelerator includes a multiple-stage vacuum system, each stage of the system including a vacuum pump and each stage directing individual aerosol particles along the particle path;

an optical detector, disposed along the particle path, that detects the speed of individual aerosol particles traveling along the path, the detected speed of each particle indicating the particle's aerodynamic size;

a laser oriented to direct a beam of light across the particle path, downstream of the optical detector;

a controller that controls the laser to direct the beam of light across the particle path coincident with the arrival of individual aerosol particles, such that each particle is desorbed into its component molecules; and a mass spectrometer that determines the chemical composition of the component molecules associated with each desorbed particle;

wherein the multiple-stage vacuum system includes a plurality of concentric tubes supporting a vacuum of progressively increasing amount, the plurality of concentric tubes being separated from each other by skimmers aligned along the particle path and being configured to be adjustably movable axially relative to each other, to vary the distances between the successive skimmers, along the particle path.

30. Apparatus for determining the size and chemical composition of individual aerosol particles, in real time, comprising:

a particle accelerator that directs a succession of individual aerosol particles along a predetermined particle path;

an optical detector, disposed along the particle path, that detects the speed of individual aerosol particles traveling along the path, the detected speed of each particle indicating the particle's aerodynamic size;

a laser oriented to direct a beam of light across the particle path, downstream of the optical detector;

a controller that controls the laser to direct the beam of light across the particle path coincident with the arrival of individual aerosol particles, such that each particle is desorbed into its component molecules; and a mass spectrometer that determines the chemical composition of the component molecules associated with each desorbed particle;

wherein the optical detector includes
 a first light source that directs a first beam of light across the particle path, at a first predetermined location,
 a first detector that detects light scattered from the particle path due to impingement of the first beam of light on an aerosol particle traveling along the path,
 a second light source that directs a second beam of light across the particle path, at a second predetermined location, downstream of the first predetermined location,
 a second detector that detects light scattered from the particle path due to impingement of the second beam of light on an aerosol particle traveling along ht path, and
 a timing device for measuring the time delay between detection of scattered light by the first detector and detection of scattered light by the second detector, such time delay indicating the speed of the associated particle;
and wherein the first and second light sources together include
 a laser that generates a laser beam having multiple wavelengths, and
 an optical assembly that separates the laser beam into the first and second beams of light, each having a wavelength different from the other, and that directs the first and second beams of light across the particle path, at the respective first and second predetermined locations.

31. Apparatus for determining the size and chemical composition of individual aerosol particles, in real time, comprising:
 a particle accelerator that directs a succession of individual aerosol particles along a predetermined particle path;
 an optical detector, disposed along the particle path, that detects the speed of individual aerosol particles traveling along the path, the detected speed of each particle indicating the particle's aerodynamic size;
 a laser oriented to direct a beam of light across the particle path, downstream of the optical detector;
 a controller that controls the laser to direct the beam of light across the particle path coincident with the arrival of individual aerosol particles, such that each particle is desorbed into its component molecules; and
 a mass spectrometer that determines the chemical composition of the component molecules associated with each desorbed particle;
 wherein the optical detector includes
  a first light source that directs a first beam of light across the particle path, at a first predetermined location,
  a first detector that detects light scattered from the particle path due to impingement of the first beam of light on an aerosol particle traveling along the path,
  a second light source that directs a second beam of light across the particle path, at a second predetermined location, downstream of the first predetermined location,
  a second detector that detects light scattered from the particle path due to impingement of the second beam of light on an aerosol particle traveling along the path, and
  a timing device for measuring the time delay between detection of scattered light by the first detector and detection of scattered light by the second detector, such time delay indicating the speed of the associated particle;
 and wherein the first and second light sources direct the respective first and second beams of light along paths that are substantially perpendicular to each other and that are in transverse planes that are substantially perpendicular to the particle path, such that aerosol particles are impinged on by both beams only if they travel along the center of the particle path.

32. Apparatus as defined in claim 31, wherein:
 the first detector includes a first photodetector oriented to detect light received in the transverse plane of the first beam of light, from the direction of the particle path, at a predetermined angle relative to the path of the first beam of light; and
 the second detector includes a second photodetector oriented to detect light received in the transverse plane of the second beam of light, from the direction of the particle path, at a predetermined angle relative to the path of the second beam of light.

33. Apparatus as defined in claim 32, wherein the predetermined angles between the path of the first beam of light and the path of light received by the first by the first photodetector, and between the path of the second beam of the light and path of the light received by the second photodetector both are about 30 degrees.

34. Apparatus for determining the size and chemical composition of individual aerosol particles, in real time, comprising:
 means for directing a succession of individual aerosol particles along a predetermined particle path, wherein the means for directing includes a multiple-stage vacuum system, each stage of the system including a vacuum pump and each stage directing individual along the particles along the particle path;
 means for detecting the location and size of individual aerosol particles traveling along the particle path;
 laser means for directing a beam of light at the successive aerosol particles, to desorb each particle into its component molecules and to ionize at least a portion of such molecules; and
 mass spectrometer means for determining the chemical composition of the ionized molecules associated with each desorbed particle;
 wherein the multi-stage vacuum system includes a plurality of concentric tubes supporting a vacuum of progressively increasing among, such tubes being separated from each other by skimmers aligned along the particle path and being configured to be adjustably movable axially relative to each other, to vary the distances between the successive skimmers, along the particle path.

35. Apparatus for determining the size and chemical composition of individual aerosol particles, in real time, comprising:
 means for directing a succession of individual aerosol particles along a predetermined particle path;
 means for detecting the location and size of individual aerosol particles traveling along the particle path;
 laser means for directing a beam of light at the successive aerosol particles, to desorb each particle into its component molecules and to ionize at least a portion of such molecules; and
 mass spectrometer means for determining the chemical composition of the ionized molecules associated with each desorbed particle;

wherein the means for detecting includes
first detection means for directing a first beam of light across the particle path, at a first predetermined location, and for detecting light scattered from the particle path due to impingement of first beam of light on an aerosol particle traveling along the path,
second detection means for directing a second beam of light across the particle path, at a second predetermined location, downstream of the first predetermined location, and for detecting light scattered from the particle path due to impingement of the second beam of light on an aerosol particle traveling along the path, and
timing means for measuring the time delay between detection of scattered light by the first detection means and detection of scattered light by the second detection means, such time delay indicating the speed, and thus the aerodynamic size, of the associated particle;
wherein the first and second detection means together include
a laser that generates a laser beam having multiple wavelengths, and
an optical assembly that separates the laser beam into the first and second beams of light, each having a wavelength different from the other, and that directs the first and second beams of light across the particle path, at the respective first and second predetermined locations.

36. Apparatus for determining the size and chemical composition of individual aerosol particles, in real time, comprising:
means for directing a succession of individual aerosol particles along a predetermined particle path;
means for detecting the location and size of individual aerosol particles traveling along the particle path;
laser means for directing a beam of light at the successive aerosol particles, to desorb each particle into its component molecules and to ionize at least a portion of such molecules; and
mass spectrometer means for determining the chemical composition of the ionized molecules associated with each desorbed particle;
wherein the means for detecting includes
first detection means for directing a first beam of light across the particle path, at a first predetermined location, and for detecting light scattered from the particle path due to impingement of the first beam of light on an aerosol particle traveling along the path,
second detection means for directing a second beam of light across the particle path, at a second predetermined location, downstream of the first predetermined location, and for detecting light scattered from the particle path due to impingement of the second beam of light on an aerosol particle traveling along the path, and
timing means for measuring the time delay between detection of scattered light by the first detection means and detection of scattered light by the second detection means, such time delay indicating the speed, and thus the aerodynamic size, of the associated particle;
and wherein the first and second detection means are configured to direct the respective first and second beams of light along paths that are substantially perpendicular to each other and that are in transverse planes oriented substantially perpendicular to the particle path, such that aerosol particles are impinged on by both beams only if they travel along the particle path.

37. A method for determining the size and chemical composition of individual aerosol particles, in real time, comprising:
using a multiple-stage vacuum system to direct a succession of individual aerosol particles along a predetermined particle path, wherein the successive stages of the vacuum system are separated from each other by skimmers aligned along the particle path;
adjustably moving the skimmers axially relative to each other, to vary the distances therebetween, along the particle path;
detecting the location and aerodynamic size of individual aerosol particles traveling along the particle path;
directing a collimated beam of light at the successive aerosol particles, to desorb each particle into its component molecules and to ionize at least a portion of such molecules; and
determining the chemical composition of the ionized molecules associated with each desorbed particle.

38. A method for determining the size and chemical composition of individual aerosol particles, in real time, comprising:
directing a succession of individual aerosol particles along a predetermined particle path;
detecting the location and aerodynamic size of individual aerosol particles traveling along the particle path, wherein detecting includes
directing a first beam of light across the particle path, at a first predetermined location, and detecting light scattered from the particle path due to impingement of the first beam of light on an aerosol particle traveling along the path,
directing a second beam of light across the particle path, at a second predetermined location, downstream of the first predetermined location, and detecting light scattered from the particle path due to impingement of the second beam of light on an aerosol particle traveling along the path, and
measuring the time delay between detection of scattered light from the first beam of light and detecting scattered light from the second beam of light, such time delay indicating the speed, and thus the aerodynamic size, of the associated particle,
wherein directing the first and second beams of light together include generating a laser beam having multiple wavelengths and separating the laser beam into the first and second beams of light, each having a wavelength different from the other;
directing a collimated beam of light at the successive aerosol particles, to desorb each particle into its component molecules and to ionize at least a portion of such molecules; and
determining the chemical composition of the ionized molecules associated with each desorbed particle.

39. A method as defined in claim 38, wherein directing the first and second beams of light includes directing the beams along paths that are substantially perpendicular to each other and that are in transverse planes oriented substantially perpendicular to the particle path, such that aerosol particles are impinged on by both beams only if they travel along the center of the particle path.

* * * * *